(12) United States Patent
Sherry et al.

(10) Patent No.: US 8,124,124 B2
(45) Date of Patent: Feb. 28, 2012

(54) COMPRESSED TABLET FORMULATION COMPRISING NON-STEROIDAL ANTI-INFLAMMATORY DRUGS AND METHODS

(75) Inventors: Robert Arthur Sherry, Nottingham (GB); Tracey Jane Rhoades, Nottingham (GB); Frederick Raymond Higton, Nottingham (GB)

(73) Assignee: Reckitt Benckiser Healthcare (UK) Limited, Slough, Berkshire (GB)

( * ) Notice: Subject to any disclaimer, the term of this patent is extended or adjusted under 35 U.S.C. 154(b) by 376 days.

(21) Appl. No.: 10/148,206

(22) PCT Filed: Nov. 30, 2000

(86) PCT No.: PCT/EP00/12193
§ 371 (c)(1),
(2), (4) Date: Aug. 30, 2002

(87) PCT Pub. No.: WO01/41733
PCT Pub. Date: Jun. 14, 2001

(65) Prior Publication Data
US 2003/0203026 A1     Oct. 30, 2003

(30) Foreign Application Priority Data

Dec. 9, 1999   (GB) .................................. 9929077.7
Dec. 9, 1999   (GB) .................................. 9929078.5

(51) Int. Cl.
    *A61K 9/20*    (2006.01)
    *A61K 9/26*    (2006.01)
    *A61K 31/192*    (2006.01)
(52) U.S. Cl. .......................... 424/464; 424/469; 514/570
(58) Field of Classification Search .................. 424/464, 424/465, 470, 469; 514/570
See application file for complete search history.

(56) References Cited

U.S. PATENT DOCUMENTS

| 5,240,712 | A | * | 8/1993 | Smith et al. ................... 424/451 |
| 5,667,807 | A | * | 9/1997 | Hurner et al. ................ 424/489 |
| 5,869,101 | A | * | 2/1999 | Moller et al. ................ 424/489 |
| 6,318,650 | B1 | * | 11/2001 | Breitenbach et al. ........... 241/23 |

FOREIGN PATENT DOCUMENTS

| EP | 0 172 014 | | 2/1986 |
| EP | 0 305 356 | | 3/1989 |
| EP | 0 362 728 | | 4/1990 |
| EP | 0 904 781 A2 | * | 3/1999 |
| JP | 56-120616 | * | 9/1981 |
| JP | 56120616 | | 9/1981 |
| JP | 05-112445 | * | 5/1993 |
| WO | WO 91/15194 | | 10/1991 |
| WO | 94 10993 | | 5/1994 |
| WO | 98 34612 | | 8/1998 |
| WO | WO 98/34612 | | 8/1998 |
| WO | WO 98/52539 | | 11/1998 |

* cited by examiner

*Primary Examiner* — Robert A Wax
*Assistant Examiner* — Aradhana Sasan
(74) *Attorney, Agent, or Firm* — Ryan A. Schneider; Troy S. Kleckley; Troutman Sanders LLP

(57) ABSTRACT

A compressed tablet composition comprising: a granular component comprising a plurality of solidified melt granules of a non-steroidal anti-inflammatory drug (NSAID) having a melting point in the range 30-300° C. and incorporating a disintegrant uniformly dispersed therein; characterised in that the granules comprise a continuous phase of said non-steroidal anti-inflammatory drug and further characterised in that the tablet composition comprises silicon dioxide present in an amount of 0.05-5.0% by weight of the composition. Preferably, the composition also contains an extra-granular component comprising the silicon dioxide and a lubricant. Further preferably the NSAID is ibuprofen which has a melting point in the range 75-77° C. Optionally the melting process can be carried out in an extruder. Tablets containing advantageous processing properties and dissolution characteristics are obtained.

53 Claims, No Drawings

COMPRESSED TABLET FORMULATION COMPRISING NON-STEROIDAL ANTI-INFLAMMATORY DRUGS AND METHODS

CROSS-REFERENCE TO RELATED APPLICATION

This application is a National Stage entry of International Application No. PCT/EP00/12193, filed Nov. 30, 2000, the entire specification claims and drawings of which are incorporated herewith by reference.

This invention relates to compositions containing a non-steroidal anti-inflammatory drug, to processes to prepare them and to uses thereof.

Non-steroidal anti-inflammatory drugs (NSAIDs) are a widely used class of medicaments. They are a well defined group of compounds and include phenylpropionic acids such as ibuprofen, naproxen, ketoprofen and flurbiprofen. They are primarily used for the treatment of one or more of pain, inflammation and fever, for example rheumatoid arthritis, ankylosing spondylitis, osteoarthritis, post-operative pain, post-partum pain and soft tissue injuries. One example is ibuprofen, which is available under prescription in the UK (eg Brufen (RTM)), generally at doses up to 3200 mg per day. Ibuprofen is also available as a non-prescription drug in the UK (eg Nurofen (RTM)) primarily for the treatment of symptoms of pain and fever including headache, migraine, rheumatic pain, muscular pain, backache, neuralgia, dysmenorrhoea, dental pain and colds and flu, generally at doses up to 1200 mg per day.

Ibuprofen and other NSAIDs are generally acidic and substantially insoluble drugs. They are conveniently administered as an oral pharmaceutical composition in the form of tablets. Thus pharmaceutically acceptable excipients must be chosen for combination with the NSAID, with which the NSAID is compatible and with which it can form tablets having a satisfactory hardness and also release the medicament rapidly into the body so that it is available for absorption.

A major issue in connection with the disorders identified above is to improve the onset of action of the NSAID, particularly in the treatment of pain. It is believed that rapid disintegration of a formulation releases the drug into the body quickly leading to a more rapid onset of therapeutic action compared with a standard dosage form. Accordingly, it is desired to produce a solid dosage form for oral administration adapted to disintegrate quickly in the gastro-intestinal tract. Many of the NSAIDs are acidic drugs, accordingly, absorption can be a problem in the acidic conditions encountered in the stomach. Furthermore, although the literature has proposed many formulations adapted to disintegrate quickly, a major problem occurs with ibuprofen and other NSAIDs as they can be administered in relatively high doses, eg up to 800 mg per unit dose. Thus, there is a problem to provide a dosage form which includes the NSAID together with excipients useful to formulate the tablet into the dosage form and also excipients useful to ensure rapid disintegration, but not to provide a tablet that is too large for patient consumption or cannot be produced according to standard large scale manufacturing processes. Furthermore, the solid dosage form must be sufficiently hard to withstand the rigours of the manufacturing process (for example as encountered during the stage of film coating in a perforated rotating drum and packaging etc) but must have appropriate disintegration characteristics to ensure rapid release of the drug from the formulation and also appropriate dissolution characteristics. Another significant problem that must be overcome is to ensure that the composition is capable of being compressed without sticking to the punches of the tabletting machine.

As an alternative to the general path of choosing particular excipients and tabletting conditions or changing the form of the unit dose, one avenue for investigation is to consider modifying the crystalline form of the NSAID in order to try to optimise its performance.

Earlier patent applications have considered heating ibuprofen, a relatively low melting drug, until molten and cooling to form a granulated composition, combining with optional tabletting excipients and compressing into a tablet. Japanese Patent Kokai 81/120616 (1981) describes a process to prepare ibuprofen granules which allows the formation of smaller dosage forms, together with better flow properties of the granulate material prior to tabletting. In the illustrative examples of JP 81/120616, the ibuprofen is melted by heating and excipients such as fine crystalline cellulose and calcium stearate are added (optionally with hydroxypropyl starch) to form a dispersion of the insoluble ingredients within the molten ibuprofen. The mixture is then cooled and crushed to form granules. The granules are either directly compressed into tablets without the addition of further excipients or mixed with Aerosil (colloidal silicon dioxide) and filled into capsules. However, it was shown by measurements of blood concentration that although smaller dosage forms and better flowability were achieved, there was no significant difference in the bioavailability between tablets prepared as described in JPA 81/120616 and those of the art available before 1981.

European Patent Application 362728 (1990) relates to an easily flowable ibuprofen granular composition that has improved storage and formulation properties for direct tabletting. The molten ibuprofen is solidified on a contact cooling apparatus using a seeding process and is then comminuted into a solid. The granulate formed consists wholly of ibuprofen. The process described requires the molten ibuprofen to be rapidly congealed under specific conditions and then seeded when the molten ibuprofen solidifies, the resulting flakes being crushed under specific milling conditions. The illustrative examples describe taking granules formed by this process and combining them with a significant amount of necessary tabletting excipients such as microcrystalline cellulose, sodium starch glycolate, colloidal silicon dioxide and magnesium stearate and compressing into tablets. In order to reduce the size of the tablet it is desired to reduce the quantity of extra-granular excipients necessary for combination with the ibuprofen granules prior to tabletting.

U.S. Pat. No. 5,240,712 (1993) discloses that molten ibuprofen may be poured into capsules and gives examples of encapsulated dosage forms containing ibuprofen, optionally containing excipients as a solid solution or dispersion therein. The molten ibuprofen composition is filled into a capsule and then allowed to solidify. The dosage forms thus produced need no further processing and can be directly administered to a patient. However, the capsules are of significant size and it is desired to produce a solid dosage form of relatively small size.

U.S. Pat. No. 5,667,807 (1997) also relates to heating ibuprofen until molten and producing tablets from the granular composition obtained therefrom. It contains illustrative examples of tablets produced firstly by forming a mixture of ibuprofen with excipients (including microcrystalline cellulose, maize starch, magnesium stearate and optionally colloidal silicon dioxide and croscarmellose sodium), and then heating and extruding said mixture in a melt extruder to produce an extrudate in which a part of the active is melted. It is said that the low melting point active fulfils the function of a binder or of a solid solvent. In a second part of the process, the cooled, comminuted granules prepared from the extrudate are compressed into tablets after the optional inclusion of a lubricant. However, it is desired to reduce the number of excipients needing to be incorporated into the composition and to improve the performance of the tablet.

WO 99/40943 discloses forming active agent/surfactant combinations using selected processing conditions to at least partially place a eutectic of the active agent/surfactant combination into intimate contact with particles of the active. The combinations are heated and subjected to force, for example by processing in an extruder. However, the amount of excipient used contributes to increasing the size of the tablets produced therefrom.

Thus, in formulating a dosage form with granules produced by solidifying molten ibuprofen, it has previously been proposed that either (a) a significant number of excipients are added to the molten ibuprofen and the granules are taken for direct compression into tablets or (b) granules containing only ibuprofen are combined with a significant amount of additional tabletting excipients then compressed into tablets.

We have now found that if a disintegrating agent is incorporated into a molten NSAID and intimately combined therewith and then is cooled and milled to produce a granule, a composition capable of tabletting with minimum tabletting excipients and having advantageous tabletting, disintegration and dissolution properties is provided, if silicon dioxide is incorporated therein.

Accordingly, the present invention provides a compressed tablet composition comprising:
a granular component comprising a plurality of solidified melt granules of a non-steroidal anti-inflammatory drug (NSAID) having a melting point in the range 30-300° C. and incorporating a disintegrant uniformly dispersed therein;
characterised in that the granules comprise a continuous phase of said non-steroidal anti-inflammatory drug and further characterised in that the tablet composition comprises silicon dioxide present in an amount of 0.05-5.0% by weight of the composition.

It has been found that formulations prepared according to the present invention have valuable disintegrating properties. Furthermore, the dissolution results show an unexpectedly high level of the NSAID dissolved in the aqueous medium after relatively short periods of time.

A further advantage of the present invention lies in the small amount of additional tabletting excipients needed to prepare a dosage form, thus leading to advantages in processing and cost of the tablets and allowing smaller dosage forms to be produced. Furthermore, the composition formed prior to tabletting has good flow properties and the resulting tablets have a good hardness.

The surface area of the NSAID in the melt granule is significantly greater than that of conventional crystals of the NSAID. In addition, the particle size is less than the particle size produced by micronising NSAID particles which is a conventionally favoured method of improving the dissolution. It is surprising that the effect of the small amounts of silicon dioxide has the effect of causing the composition to disperse so quickly in aqueous conditions, especially in acidic conditions (such as are found in the stomach) leading to a high percentage of NSAID being dissolved within a relatively short period.

The invention allows the formulation of any relatively low melting NSAID into an acceptably tasting, readily disintegrating composition. A favoured class of compounds are the 2-arylpropionic acids which are generally substantially insoluble and have poor taste properties. It is generally envisaged that the melting point of such compounds will be low enough to allow the melting thereof using standard equipment. It is also important that there is not a deleterious effect on the ingredients incorporated in the molten NSAID, for example the disintegrant. Thus, typical melting points of the low melting NSAIDs would be expected to fall within the range 30-300° C. Preferred NSAIDs have lower melting points so that the melting process does not use significant amounts of energy, which thus has an effect on production costs. Preferred melting points are in the range 30-200° C. (such as racemic naproxen, melting point 156° C.), more preferably 30-150° C., further preferably 40-120° C. (such as racemic flurbiprofen, melting point 114° C.), most preferably 50-100° C. (such as racemic ibuprofen (melting point 75-77° C.), S(+)-ibuprofen (melting point 52-54° C.) and racemic ketoprofen (melting point 96° C.)). Preferred low-melting NSAIDs are naproxen, ketoprofen, flurbiprofen, ibuprofen or enantiomers (especially the S(+)-enantiomers) thereof. The invention is especially adapted for an ibuprofen medicament. The term "ibuprofen medicament" includes racemic ibuprofen and S(+)-ibuprofen which have low melting points and a very poor after-taste in the mouth and throat. Most advantageous results are obtained with racemic ibuprofen which has a high dosage combined with poor solubility properties.

The proportion of NSAID in the granular composition will depend on the dose desired for therapeutic effect. Low dose drugs, such as flurbiprofen and ketoprofen may form as little as 20% by weight (for example 20-99%) of the composition in order to provide that the tablet is not too small. However, a preferred feature of the invention is that low-melting, high dose NSAIDs, such as ibuprofen, can be formulated into smaller dosage forms. Accordingly, the NSAID will suitably form greater than 70% w/w of the granular component (for example 70-99% by weight), preferably 70-95%, further preferably 75-85% w/w of the granular component. The NSAID will suitably form greater than 50% by weight of the tablet composition, for example 60-97% by weight, preferably 70-95% by weight, more preferably 70-90% by weight and most preferably 75-85% by weight of the composition.

The disintegrating agent has the effect of causing an NSAID tablet composition to disintegrate under the conditions found in the gastro-intestinal tract. Examples of disintegrating agents include one or more of wheat starch, maize starch, potato starch, sodium starch glycolate, low-substituted hydroxypropyl cellulose, alginic acid, cross-linked polyvinylpyrrolidone, magnesium aluminium silicate and croscarmellose sodium. Preferred disintegrating agents are those which swell on the action of water thus causing the ingredients in the tablet to be pushed apart and out into the aqueous disintegration medium. Preferred disintegrating agents comprise one or more of croscarmellose sodium and sodium starch glycolate, especially croscarmellose sodium. The disintegrating agent is present at an effective disintegrating amount, for example up to 25% by weight of the composition, more preferably 1-25% w/w, further preferably 3-20% w/w and most preferably 8-17% by weight of the composition. The disintegrating agent will suitably form 1-25% by weight of the granular component, preferably 5-23% w/w and most preferably 8-20% by weight of the granular component.

Preferably the ratio of ibuprofen medicament to disintegrating agent in the range is 30:1 to 1:1 parts by weight, preferably 20:1 to 2:1, more preferably 10:1 to 3:1 parts by weight.

The silicon dioxide is insoluble and suitably has a surface area greater than 50 $m^2g^{-1}$, more preferably greater than 100 $m^2g^{-1}$, especially in the range 150-250 $m^2g^{-1}$. Most preferably the silicon dioxide is colloidal silicon dioxide (especially having a mean particle size less than 50 nm such as 5-40 nm), most preferably anhydrous colloidal silicon dioxide. The tapped density of the silicon dioxide is preferably in the range 0.01-0.2 gcm$^{-2}$.

The silicon dioxide is incorporated in the composition to an extent of 0.05-5.0% by weight (preferably 0.1-3% by weight, more preferably 0.2-1% by weight) of the composition. The silicon dioxide may be incorporated in the granules. Preferably, if incorporated in the granules, it is used to an extent of 0.1-1%, more preferably 0.2-0.8% by weight of composition.

In the preparation of the granular component, the NSAID is melted. Under pressurised conditions, the drug may be melted at a temperature below its normal melting point. Melting may be carried out according to known methods, including for example, heating in a vessel to a temperature above the melting point of the NSAID or by extrusion in a heated extruder. The maximum temperature is determined by the stability of the molten drug and ingredients combined therewith. The drug may be heated to any convenient temperature. Generally, the higher the temperature, the more quickly the drug will melt although this must be balanced by the energy input required to heat the drug. For highest efficiency, it is generally envisaged that the NSAID will be heated to not more than 25° C., preferably 5-10° C., above its melting point to keep energy costs to a minimum. Thus, a preferred heating range is 30-180° C., more preferably 35-140° C. and further preferably 40-120° C. If the NSAID is extruded, generally the extruder is heated to a given temperature. In addition, the work on the NSAID by the screw configuration in the extruder will also contribute to melting the NSAID thereby reducing its external applied temperature requirement. Accordingly the extruder barrel may be heated to a temperature less than the melting point of the NSAID. For example, the normal melting point of racemic ibuprofen is 75-77° C., however under conditions of force/pressure (such as may be encountered in an extruder or similar processing device), the external applied heat necessary to melt the ibuprofen may be reduced significantly through the mechanical heat generated by the intense mixing action within the extruder. It is generally envisaged that the extruder will be heated to a temperature not less than 25° C. below the melting point of the drug, preferably in the range from 15° C. below the melting point of the drug to 25° C. above the melting point of the drug, more preferably to a temperature in the range of 10° C. on each side of the melting point of the drug. Some extruders allow different zones to be heated to different temperatures in the extruder. These temperatures can be chosen as desired to ensure that the NSAID is fully melted.

When the NSAID is ibuprofen it may conveniently be heated in the range 50-100° C., more preferably 60-100° C. When heated by conventional heating means such as a water or steam bath it is preferably heated in the range 75-90° C., more preferably 75-85° C. The ibuprofen may also be heated and subjected to conditions of force, such as by heat-extruding the ibuprofen, for example in a twin-screw extruder. The temperature of the ibuprofen in the extruder barrel is preferably in the range 66-96° C., preferably 70-82° C.

When the NSAID is substantially fully melted, a liquid is formed. The NSAID should be fully melted so that on cooling, a single continuous phase of the NSAID is formed. The disintegrant is combined with the melted NSAID, either prior to melting or after the melting process. The disintegrant is most commonly insoluble in the ibuprofen melt and a dispersion of the solid disintegrating agent within the liquid melt is produced. The dispersion is mixed so that the disintegrating agent is uniformly or homogeneously combined with the melted NSAID. A uniform mixture is thus produced. The mixture is allowed to cool by methods hereinafter discussed until a solid is produced. As the mixture cools, it becomes more viscous. The NSAID which solidifies is then formed into melt granules. Thus, as used herein, "solidified melt granules" means granules formed by combining the NSAID in fully molten form with a disintegrant and other optional tabletting excipients, cooling to a temperature below the melting point of the NSAID and forming the solid mass into granules. The granular composition comprises a plurality of such granules.

The melt is allowed to solidify in any manner found convenient. This includes both rapid cooling and slow cooling. For example, the molten NSAID may be allowed to cool overnight at ordinary temperatures or in a cooled vessel. The molten NSAID may be poured onto cooling trays which may be static or continuously moving. Static trays may be placed in cooling cabinets. Moving trays or belts may have additional cooling means, such as cooled water. The cooled melt forms a solid and may be scraped off the belt or collected as it falls off one end of a continuously moving belt.

The solidified melt incorporating the disintegrant may be formed into granules by a plurality of methods. For example, it may be pulverised into granules. It may be milled and/or sieved. It may also be passed through a spray device such as a spray tower or spray granulator in which the molten material is sprayed from an orifice into a stream of cooled air, allowed to congeal/solidify and then collected. If the molten NSAID is extruded, the extrudate may be cooled and then broken into conveniently sized pieces, followed by milling and or sieving. Alternatively, the extrudate may be extruded through holes and chopped into suitably sized granules for tabletting.

The NSAID forms a continuous phase in the granule. That is to say the crystalline structure of the NSAID is not interrupted by another crystalline structure. This may occur, for example, if the NSAID is only partially melted where the crystalline structure of the melted NSAID is interrupted by the non-melted NSAID, thus providing that the NSAID does not have a single crystalline structure. The crystalline structure of the solidified melted NSAID is different from the crystalline structure of unmelted NSAID, for example in terms of particle size. Thus, in compositions according to the present invention, the NSAID is present in a single crystalline state and thus the NSAID continuous phase comprises a single crystalline phase of the NSAID.

Although not necessary for the carrying out of the present invention, if desired the compressed tablet composition may comprise additional excipients.

For example, the composition may comprise a proportion of water-soluble or water-insoluble diluent. Suitable water-soluble diluent materials include the sugar alcohols (such as xylitol, sorbitol, mannitol, erythritol), sugars (such as sucrose, fructose, lactose, dextrose), cyclodextrin, maltodextrin and salts of organic acids (eg sodium citrate and potassium citrate). Lactose, sodium citrate and potassium citrate are particularly preferred water-soluble diluents. Suitable water-insoluble diluent materials include cellulose derivatives (such as microcrystalline cellulose) starch and derivatives thereof (such as pre-gelatinised starch), dicalcium phosphate, tricalcium phosphate, calcium sulphate, calcium carbonate. Microcrystalline cellulose and dicalcium phosphate are preferred water insoluble diluents. In a tablet adapted to disperse in water prior to administration, the level of diluent may be quite high, for example up to 50% (such as 0-50% w/w, preferably 0-40% w/w) by weight of the composition in order to achieve the desired dispersing properties. Preferably, in tablets for oral administration, the diluent does not form greater than 25% by weight of the composition (eg 0-25% w/w), as it adds to the costs of the composition and to production costs. Thus, to minimise costs it may be preferred that the diluent is added to the composition in an amount of 0-20% by weight of the composition, more preferably 0-10% w/w. If present, it may be preferably used to an extent of 0.1-25% by weight of the composition, more preferably 0.1-20% w/w, further preferably 0.1-10% w/w and most preferably 1-5% by weight of the composition.

The diluent may preferably include a basic ingredient such as an alkali metal salt for example an alkali metal carbonate, bicarbonate or citrate, present to an extent of up to 50% by weight (eg in the range 1-50% by weight), preferably up to 40% by weight (eg in the range 1-40% by weight) of the composition (more preferably 2-35% w/w and most preferably 10-20% w/w). Preferably, the alkali metal salt is sodium or potassium. Further preferably, the salt is a citrate, carbonate or bicarbonate salt of sodium or potassium, more preferably sodium bicarbonate or citrate. The ratio of NSAID (especially ibuprofen medicament) to alkali metal salt may be in the range 100:1 to 1:1 parts by weight, preferably 5:1 to 1:1 parts by weight. Preferably, the alkali metal salt is incorporated in any amount up to an equimolar amount with respect to the NSAID (eg ibuprofen). Conveniently, a sub-molar amount of alkali metal salt is incorporated. Thus the alkali metal compound may form up to 100% w/w of the NSAID, preferably 50% w/w, more preferably up to 10% w/w, of the NSAID. In a preferred compressed tablet according to the present invention, the NSAID (especially an ibuprofen medicament) is in admixture with the alkali metal salt. The alkali metal salt is preferably incorporated into the extra-granular component for admixture with the granular component prior to compression into a tablet.

The granular component may also include a surfactant, in an amount appropriate to the properties of the surfactant, preferably 0.05-10% by weight of the composition. Preferred surfactants are sodium lauryl sulphate and poloxamer. They may be used to an extent of 0.05-8% by weight (preferably 0.1-5% by weight, more preferably 0.2-2% by weight) of the composition.

A preferred granular component comprises an NSAID (preferably ibuprofen), a disintegrant, a surfactant and optionally a diluent. A further preferred granular component consists essentially of an NSAID (preferably ibuprofen), a disintegrant and a surfactant. A further preferred granular component consists essentially of an NSAID (preferably ibuprofen), a disintegrant, a surfactant and a diluent.

The melt granules in the granular composition preferably have a mean particle size in the range 10-2000 μm, more preferably 50-1000 μm and most preferably 100-400 μm. Valuable results are achieved when the bulk density of the melt granules is in the range 0.1-1 $gml^{-1}$, more preferably 0.3-0.6 $gml^{-1}$. Further preferred properties are obtained when the tapped density is in the range 0.3-0.7 $gml^{-1}$ (more preferably 0.4-0.6 $gml^{-1}$).

In a composition according to the present invention, it is preferred that the granular component of melt granules is combined with an extra-granular component. Preferably the composition comprises a granular component in an amount of 60-99.95% (more preferably 70-99.9% by weight, especially 75-99.9% by weight, particularly 80-99.9% and most preferably 95-99.9% by weight) and 0.05-40% extra-granular component (preferably 0.1-30%, especially 0.1-25%, particularly 0.1-20%, and most preferably 0.1-5%) by weight of the composition.

The extra-granular component comprises the ingredients incorporated in the compressed tablet which are not contained in the solidified melt granules. They may be mixed with the melt granules simultaneously or at sequential stages in the process to prepare the tablets. A particular advantage of the present invention is preferably that all the ingredients of the extra-granular component are combined with the granular component at the same time and also that there does not have to be significant processing of the ingredients in the extra-granular component prior to combining with the granular compound. The compressed tablet comprises a uniform mixture of granular component and extra-granular component. The extra-granular component is suitably distributed evenly throughout the composition.

A preferred compressed tablet composition of the present invention comprises:
a) 60-99% granular component by weight of the composition, said granular component incorporating 0.005-1 parts by weight disintegrant per part by weight of non-steroidal anti-inflammatory drug; and
b) 0.05-40% extra-granular component by weight of the composition.

Preferably, the silicon dioxide is present in the extra-granular component. Further preferably, the silicon dioxide is present in the extra-granular component to an extent of 0.1-3%, more preferably 0.2-2% by weight of the composition.

Optionally a lubricant may be incorporated in the extra-granular component for mixing with the granular component. Conventional lubricants for ibuprofen tablets may be used for example stearic acid, sodium lauryl sulphate, polyethylene glycol, hydrogenated vegetable oil, sodium stearyl fumarate, magnesium stearate or calcium stearate. These may be present in an amount from 0.05-5% by weight, preferably 0.1-2% by weight of the composition. Anti-adherents such as talc, may further be included in an amount of up to 4% by weight of the dosage form, for example 0.5-2% by weight of the dosage form, preferably as part of the extra-granular component.

An advantageous tablet composition according to the present invention comprises an extra-granular component comprising silicon dioxide and a lubricant. This may form an intimate admixture with said granular component prior to compression into a tablet. Preferably, the extra-granular component consists essentially of silicon dioxide and a lubricant in a ratio of one part by weight silicon dioxide to 0.5-5 parts by weight lubricant, more preferably 0.5-2 parts by weight lubricant.

Although not necessary for the production of compositions according to the present invention, if desired, the dosage form may further comprise tabletting excipients such as a compressible diluent. This may be contained in the melt granule (as discussed above) or may be combined with the extra-granular ingredients prior to compression as part of the extra-granular component or may be incorporated as desired in both components. Examples of such compressible diluents include one or more of a cellulose derivative (such as microcrystalline cellulose), starch and derivatives thereof (eg pre-gelatinised starch), soluble sugars (eg lactose, fructose, dextrose, sucrose, dextrin), sugar alcohols (eg xylitol, sorbitol, mannitol, erythritol), sodium chloride, dicalcium phosphate, tricalcium phosphate, calcium sulphate, mannitol, sorbitol, cyclodextrin, and maltodextrin and salts of organic acids (e.g. sodium citrate and potassium citrate). Microcrystalline cellulose and the salts of organic acids are preferred as hereinabove discussed.

If necessary for tabletting a low dose drug, the diluent material may form up to 80% by weight of the composition. Preferably, it is used to an extent of 0-30% by weight of the composition and more preferably 0-20% of the total composition. If desired, the diluent may be added in an amount up to 30% by weight of the extra-granular component, although to minimise the size and cost of the dosage form, it is desired to include a minimum amount of such additional excipients. Accordingly, if employed, the diluent may suitably be included in the extra-granular component in the range up to 20% by weight (ie 0.1-20%), preferably 0.1-15%, more preferably 0.1-10%, desirably 1-5% by weight. As discussed hereinabove, the diluent may be present in the granular component, for example 0-20% (such as 0.1-20%) by weight of the composition and/or in the extra-granular component, for example 0-20% (such as 0.1-20%) by weight of the composition.

Other conventional tabletting excipients known to the person skilled in the art may be incorporated in the compressed tablet composition according to the present invention as desired, although it will be appreciated that a prime advantage of the present invention is that the number of excipients necessary to achieve a quickly disintegrating tablet with good dissolution characteristics is minimal.

A preferred compressed tablet composition comprises an intimate mixture of:
a) a granular component comprising a solidified melt of an ibuprofen medicament incorporating a disintegrant homogeneously dispersed therein: and
b) 0.05-5.0% silicon dioxide by weight of the composition.

In a further preferred compressed tablet composition according to the present invention, there is provided a compressed mixture of:
a) solidified melt granules comprising 70-97% ibuprofen by weight of the granule (preferably 70-95% by weight), 3-25% croscarmellose sodium by weight of the granule (preferably 5-20% by weight) and 0-20% diluent by weight of the granule (preferably 8-16% by weight) uniformly dispersed therein, the ibuprofen being present in a continuous phase;
b) 0.05-5.0% w/w silicon dioxide; and optionally
c) a lubricating agent.

In a further preferred composition according to the present invention there is provided, preferably as an intimate mixture,
a) 90-99.95% granular component by weight of the composition, said granular component comprising solidified melt granules of ibuprofen incorporating croscarmellose sodium and optionally a diluent uniformly dispersed therein, said ibuprofen being present in a single continuous phase and in an amount of 70-99% by weight of the composition, said croscarmellose sodium being present in an amount of 1-25% by weight of the composition and said diluent being present in an amount of 0-20% by weight of the composition; and
b) 0.05%-10% extra-granular component by weight of the composition comprising:
i) 0.1-3% lubricant by weight of the composition; and
ii) 0.05-2% silicon dioxide by weight of the composition.

An advantageous compressed tablet composition according to the present invention comprises a uniform blend of:
a) a granular component comprising:
i) 70-90% ibuprofen by weight of the composition, said ibuprofen being present as a continuous phase;
ii) 8-20% croscarmellose sodium by weight of the composition;
iii) 0-20% diluent by weight of the composition; and b) an extra-granular component comprising:
iv) 0.5%-2% stearic acid or a salt thereof by weight of the composition;
v) 0.1-2.5% silicon dioxide by weight of the composition the sum of components (i) to (v) being greater than 99% by weight of the composition.

Most preferably, the granular component consists essentially (ie greater than 98% by weight of the composition) of ibuprofen, croscarmellose sodium and a diluent (preferably a salt (eg an alkali metal salt) of an organic acid or microcrystalline cellulose). In a further advantageous composition, the granular component consists essentially of ibuprofen, croscarmellose sodium and a surfactant. Particular advantages are also achieved if the granular component consists essentially of ibuprofen, croscarmellose sodium, a diluent (preferably microcrystalline cellulose or an alkali metal salt of an organic acid) and a surfactant (preferably sodium lauryl sulphate or a poloxamer). For example, an advantageous composition may consist essentially of (ie greater than 98% by weight of the composition) a uniform mixture of 75-95% ibuprofen by weight of the granular composition, 5-20% disintegrant by weight of the granular composition and 0-20% diluent by weight of the granular composition, the composition comprising solidified melt granules of ibuprofen and the ibuprofen being present as a single continuous phase.

The compressed tablet composition of the present invention may, if desired, include other compatible pharmacologically active ingredients and/or enhancing agents. Thus, for example, the dosage form may include any other ingredient commonly used in a composition useful to treat pain, inflammation and/or fever, for example caffeine or another xanthine derivative, another analgesic, for example codeine, a skeletal muscle relaxant: an antihistamine (e.g. acrivastine, astemizole, azatadine, azelastine, bromodiphenhydramine, brompheniramine, carbinoxamine, cetirizine, chlorpheniramine, cyproheptadine, dexbromopheniramine, dexchlorpheniramine, diphenhydramine, ebastine, ketotifen, lodoxamide, loratidine, levocabastine, mequitazine, oxatomide, phenindamine, phenyltoloxamine, pyrilamine, setastine, tazifylline, temelastine, terfenidine, tripelennamine or triprolidine (preferably non-sedating antihistamines are employed)); a decongestant (eg pseudoephedrine, phenylpropanolamine and phenylephrine); a cough suppressant (eg caramiphen, codeine or dextromethorpan); and/or an expectorant (eg guaifenesin, potassium citrate, potassium guaiacolsuphonate, potassium sulphate and terpin hydrate).

Such extra active ingredients and/or enhancing agents may be incorporated in the melt granules or in the extra-granular component which is combined with the melt granule prior to formulation into a compressed tablet.

The present invention also provides a composition comprising a granular component consisting essentially of a uniform mixture of a low melting NSAID (especially an ibuprofen medicament) and croscarmellose sodium in the form of solidified melt granules.

In a further aspect of the present invention, there is provided a granulate comprising a plurality of solidified melt granules, said, granules comprising a continuous phase of ibuprofen and consisting essentially of a uniform mixture of 70-95% ibuprofen by weight of the granule, 5-20% disintegrant by weight of the granule and 0-20% diluent by weight of the granule. A preferred feature of the granule is the further inclusion of a surfactant.

Ibuprofen and its derivatives are primarily anti-inflammatory, analgesic and anti-pyretic agents but have also been proposed for other therapeutic uses, including the treatment of periodontal bone loss, pruritus and Alzheimer's disease.

The dosage forms of the present invention are therefore indicated for use in the treatment of all therapeutic uses for which ibuprofen is effective, including rheumatoid arthritis, osteoarthritis, ankylosing spondylitis, seronegative arthropathies, periarticular disorders and soft tissue injuries. They may also be used in the treatment of postoperative pain, postpartum pain, dental pain, dysmenorrhoea, headache, migraine, rheumatic pain, muscular pain, backache, neuralgia and/or musculoskeletal pain or the pain or discomfort associated with the following: respiratory infections, colds or influenza, gout or morning stiffness.

Accordingly, in another aspect of the present invention there is provided a composition according to the present invention for use in the treatment of pain and/or inflammation and/or fever. Furthermore, the invention also provides a method of treating pain and/or inflammation and/or fever comprising the administration of a composition according to the present invention to a mammal in need thereof.

Unit dosages for effective therapy are known to those skilled in the art for each NSAID. For example, they may comprise the NSAID to an extent of 5 mg, 10 mg, 12.5 mg, 25 mg, 50 mg, 100 mg, 150 mg, 200 mg, 250 mg, 300 mg, 350 mg, 400 mg, 500 mg, 600 mg and 800 mg. Where derivatives are employed, normally the precise unit dosages are chosen to give the equivalent NSAID doses given above. For the treatments described herein the maximum daily dose of ibuprofen is generally 3200 mg. A single unit daily dose may be 100 mg. Preferred unit doses are in the range 100-400 mg, more preferably 100-300 mg and especially 200 mg ibuprofen. The maximum daily dose of flurbiprofen is generally 300 mg. A single unit dose may be 12.5 mg. Preferred unit doses are in the range 12.5-150 mg, more preferably 25-100 mg and especially 50 mg flurbiprofen. The maximum daily dose of naproxen is generally 1500 mg. A single unit daily dose may be 125 mg. Preferred unit doses are in the range 220-750 mg, more preferably 220-500 mg and especially 220-250 mg naproxen. The maximum daily dose of ketoprofen is generally 200 mg. A single unit dose may be 25 mg. Preferred unit doses are in the range 25-100 mg, more preferably 25-75 mg and especially 50 mg ketoprofen.

The compressed tablet composition preferably comprises a combination of the granular component with an extra-granular component comprising silicon dioxide and optionally a lubricant. This combination may take the form of a uniform or homogeneous blend capable of being mixed with other ingredients as desired and compressed into tablets. The tablet composition may be swallowed or dispersed in water prior to ingestion. Preferably the tablet composition releases the ibuprofen medicament in the stomach or gastro-intestinal tract.

In a further aspect, the present invention provides use of silicon dioxide in an extra-granular component combined with a granular component in a compressed composition, said granular component comprising a plurality of solidified melt granules of a low melting (e.g. melting point is in the range 30-300° C.) non-steroidal anti-inflammatory drug incorporating a disintegrant and optionally a diluent homogeneously dispersed therethrough, the composition comprising 0.05-5% silicon dioxide by weight of the composition and the granules comprising a continuous phase of said non-steroidal anti-inflammatory drug.

In yet a further aspect, the present invention provides a process to prepare a compressed tablet composition comprising a non-steroidal anti-inflammatory drug having a melting point in the range 30-300° C. characterised by:

a) combining said drug in fully molten form with a disintegrant to form a uniform mixture;
b) cooling said mixture to form a solidified melt;
c) forming said solidified melt into granules;
d) compressing said granules, optionally with an extra-granular excipient, to form a tablet.

The disintegrating agent may be sole ingredient incorporated within the NSAID (preferably ibuprofen) melt granules or it may be combined with a diluent and optionally a surfactant and other tabletting excipients. Accordingly, the granular composition may consist essentially of (ie greater than 98% by weight of the composition) an ibuprofen medicament and disintegrating agent or it may consist of an ibuprofen medicament, a disintegrant, a diluent and optionally a surfactant. Thus the diluent and optional surfactant may be combined with the disintegrant and the drug in fully molten form. A tablet composition according to the present invention may be prepared by incorporating silicon dioxide and optionally and other excipients within the composition to be tabletted, preferably to form a powder blend, followed by compression into tablets.

The abovementioned process may be carried out in a number of ways. In one method, the NSAID is heated in a suitable vessel until molten. The disintegrating agent may then be added to the molten mass and thoroughly combined therewith to form a homogeneous mixture. Optional extra excipients may also be blended into the molten NSAID simultaneously or sequentially. The molten mixture may then be discharged into an appropriate cooling system, for example a cooled belt which may continuously rotate and deliver the cooled melt to a comminuting device such as a scraper bar and/or a mill.

In a further process, the non-steroidal anti-inflammatory drug may be combined with the disintegrant and optional tabletting excipients, eg a diluent, and then heated together until said non-steroidal anti-inflammatory drug is fully molten. In yet a further process the NSAID and disintegrant are combined and heated together until said NSAID is fully molten and any further desired tabletting excipients uniformly blended with the mixture.

In another method, the NSAID and disintegrating agent are fed into an extruder type system (preferably having first been combined by blending together). The materials are heated and mixed in the extruder until the NSAID is fully molten and a uniform mixture is produced. The NSAID and disintegrant are extruded and the extrudate cooled. Preferably, the NSAID and the disintegrant are extruded in a twin screw extruder. The hot mass (comprising the NSAID and disintegrant) extruded forms an agglomerated mass which may be collected and, if desired, milled to form granules.

In a further method, after heating or heat-extrusion the NSAID and disintegrating agent may be cooled by feeding to a spray tower dryer in which the molten mass is sprayed into the path of a stream of cold air and the dried solid mass collected.

The granular component may be tabletted directly in the absence of extra-granular component or it may be combined with an extra-granular component and fed to a tabletting machine to be compressed into tablets. Preferably the extra-granular component comprises silicon dioxide and optionally a lubricant. Further preferably, the extra-granular component comprises silicon dioxide and a lubricant.

In a preferred aspect of the present invention, there is provided a process to prepare an ibuprofen granular composition comprising melting an ibuprofen medicament (preferably ibuprofen), incorporating a disintegrating agent uniformly within the melted ibuprofen medicament, allowing said ibuprofen medicament to cool to form a solid and comminuting said melt to form a granular composition. The disintegrating agent is thus generally combined with the ibuprofen medicament to form a uniform mixture of solid disintegrating agent in the liquid ibuprofen medicament melt prior to cooling.

The compressed tablet composition of the present invention may optionally be coated with a film coat, for example based on a conventional cellulose polymer such as hydroxypropylmethylcellulose, or a conventional sugar coat, for example based on sucrose or lactose.

The granular composition, may if desired be combined with a flow acid such as silicon dioxide and filled into capsules. Advantageous dissolution results can be obtained. This does not fall within the scope of the present invention.

The invention is illustrated by the following non-limiting Examples. In the Examples, the racemic ibuprofen and racemic flurbiprofen is available from Knoll Pharma, Nottingham, GB; colloidal silicon dioxide (also known as colloidal silica) is available from Degussa, Frankfurt, DE under the trade name Aerosil 200; Croscarmellose sodium is available from the FMC Corporation, Brussels, BE under the tradename Ac-Di-Sol; and sodium starch glycolate is available from Edward Mendell, Reigate, GB under the tradename Explotab; Poloxamer is available from BASF, DE under the trade name Pluronic F68; Dicalcium phosphate is available under the trade name Emcompress; Hydrogenated Castor oil is available from BASF, DE under the trade name Cremophor RH40, Microcrystalline cellulose is available from the FMC Corporation, Brussels, BE under the trade name Avicel PH 101.

Dissolution Measurement

The dissolution was measured using the dissolution method described in the US Pharmacopoeia Vol. 23, page 1791, Apparatus 2 using paddles at 50 rpm and a phosphate buffer (selected at pH 7.2 and/or pH 6.0 and/or pH 5.8).

Friability Measurement

This test for the robustness of the tablet is a standard friability test, namely the rotation of 20 tablets for a given time period at 25 rpm in a friabulator (TAR 20 manufactured by ERWEKA). The following measurements were made:
1. The number of capped or broken tablets;
2. The % weight loss from the tablet.

Crushing Strength (N)

The crushing strength is a measure of the hardness of a tablet. It was measured by recording the diametrical crushing strength when the tablet was broken between the motorised jaws of a Schleuniger crushing strength tester. The range of crushing strengths of five tablets prepared with each Example formulation is given.

Disintegration Time (Minutes)

The disintegration time can be measured using the disintegration method described in the European Pharmacopoeia 1986, Ref V.5.1.1 (updated 1995) using tap water (pH approximately 7) as the liquid. The method provides the time by which six tablets prepared with each Example formulation disintegrates.

Granulation Apparatus

The spray granulator was the PFB 28 available from APV, Denmark. The spray tower was FBSD 66 available from APV, Denmark. The twin screw extruders were the MP19 (19 mm barrel) and MP40 PC (40 mm barrel) available from APV, UK.

EXAMPLE 1

|  | (% w/w) |
|---|---|
| Granular Component: |  |
| Ibuprofen | 93.9 |
| Croscarmellose Sodium | 4.7 |
| Extra-granular Component: |  |
| Colloidal Silica | 0.5 |
| Stearic Acid | 0.9 |

EXAMPLE 1(a)

Preparation of Granular Component

In the illustrative process, the ibuprofen was first melted by heating to approximately 75° C. in a stainless steel vessel until fully molten. The disintegrating agent (croscarmellose sodium) was then added to the molten ibuprofen and mixed for 5-10 minutes until uniformly dispersed. The molten mixture was poured onto a stainless steel tray and cooled over a period of up to 60 minutes, ensuring that the suspension was maintained. The mass thus formed was milled by passing through a cone mill having a screen with a round hole size of 1 mm. The resulting granules were collected.

EXAMPLE 1(b)

Preparation of Tablets

The basing ingredients, namely silicon dioxide and stearic acid (a lubricant) were blended simultaneously with the granular composition for approximately 15 minutes in a blender. The blended material was fed to a tabletting machine and compressed into tablets containing 200 mg ibuprofen.

EXAMPLES 2-4

|  | Ex 2 (% w/w) | Ex 3 (% w/w) | Ex 4 (% w/w) |
|---|---|---|---|
| Ibuprofen | 91.3 | 89.7 | 85.8 |
| Croscarmellose Sodium | 7.3 | 9.0 | 12.9 |
| Colloidal Silica | 0.5 | 0.4 | 0.4 |
| Stearic Acid | 0.9 | 0.9 | 0.9 |

Examples 2-4 were prepared in the same manner as described in Example 1 to produce tablets containing 200 mg ibuprofen.

EXAMPLES 5-8

|  | Ex 5 (% w/w) | Ex 6 (% w/w) | Ex 7 (% w/w) | Ex 8 (% w/w) |
| --- | --- | --- | --- | --- |
| Ibuprofen | 93.9 | 91.3 | 89.7 | 85.8 |
| Sodium Starch Glycolate | 4.7 | 7.3 | 9.0 | 12.9 |
| Colloidal Silica | 0.5 | 0.5 | 0.4 | 0.4 |
| Stearic Acid | 0.9 | 0.9 | 0.9 | 0.9 |

Examples 5-8 were prepared in the same manner as described in Example 1 except that sodium starch glycolate was used as the disintegrating agent. Tablets containing 200 mg ibuprofen were prepared.

EXAMPLES 9-12

|  | Ex 9 (% w/w) | Ex 10 (% w/w) | Ex 11 (% w/w) | Ex 12 (% w/w) |
| --- | --- | --- | --- | --- |
| Granular Component: | | | | |
| Ibuprofen | 66.2 | 73.9 | 63.3 | 86.6 |
| Croscarmellose Sodium | 5.3 | 5.9 | 5.1 | 6.9 |
| Extra-granular component: | | | | |
| Colloidal Silica | 1.0 | 1.1 | 0.6 | 1.3 |
| Stearic Acid | 0.7 | 0.7 | 0.9 | 0.9 |
| Sodium carbonate | — | 18.4 | — | — |
| Sodium Bicarbonate | 26.8 | — | — | — |
| Sodium citrate | — | — | 30.1 | 4.3 |

Examples 9-12 were prepared in the same manner as described in Example 1, except that a basic excipient (sodium citrate/sodium carbonate/sodium bicarbonate) was included in the extra-granular component for combination with the granular component. Tablets or component containing 200 mg ibuprofen were prepared. The dissolution results of tablets before storage are given in Table 1 below. Table 2 gives the dissolution results for Examples 2 and 4 after storage for 3 months at 40° C. and 75% relative humidity and shows that a good performance is maintained even on storage. Table 3 relates to the dissolution performance of Example 9 at different pH's. It shows that valuable dissolution properties are obtained even when the pH of the dissolution medium is lowered.

TABLE 1

Dissolution Results at pH 7.2 of Example 1-9 tablets before storage

| | Dissolution Time: | | | | |
| --- | --- | --- | --- | --- | --- |
| Example: | 10 mins | 20 mins | 30 mins | 45 mins | 60 mins |
| 1 | >100% | >100% | >100% | >100% | >100% |
| 2 | 98.2% | >100% | >100% | >100% | >100% |
| 3 | 88.5% | >100% | >100% | >100% | >100% |
| 4 | 84.6% | 94.4% | 95.9% | 96.0% | 96.2% |
| 5 | 87.3% | >100% | >100% | >100% | >100% |
| 6 | >100% | >100% | >100% | >100% | >100% |
| 7 | 75.0% | 98.4% | >100% | >100% | >100% |
| 8 | 88.2% | >100% | >100% | >100% | >100% |
| 9 | 89.2% | 98.4% | 98.4% | 98.8% | 98.5% |

TABLE 2

Dissolution Results at pH 7.2 on Storage of Examples 2 and 4 for 3 months at 40° C./75% Relative Humidity

| | Dissolution Time: | | | | |
| --- | --- | --- | --- | --- | --- |
| Example: | 10 mins | 20 mins | 30 mins | 45 mins | 60 mins |
| 2 | 83.9% | 97.9% | 99.4% | 99.6% | 99.3% |
| 4 | 84.5% | 91.3% | 90.5% | 92.3% | 92.3% |

TABLE 3

Example 9: Dissolution Results: pH 7.2 and 5.8

| | Dissolution Time: | | | | |
| --- | --- | --- | --- | --- | --- |
| | 10 mins | 20 mins | 30 mins | 45 mins | 60 mins |
| pH 7.2 | 89.2% | 98.4% | 98.4% | 98.8% | 98.5% |
| pH 5.8 | 46.3% | 61.6% | 69.9% | 77.5% | 83.8% |

It is noted that although at the lower pH a smaller percentage of ibuprofen is dissolved, this reflects the problems associated with the solubility of ibuprofen in an acidic medium. The valuable properties of the present formulation are shown in that over 60% of the ibuprofen has dissolved in 20 minutes, even at pH 5.8.

EXAMPLES 13-17

|  | Ex 13 (% w/w) | Ex 14 (% w/w) | Ex 15 (% w/w) | Ex 16 (% w/w) | Ex 17 (% w/w) |
| --- | --- | --- | --- | --- | --- |
| Ibuprofen | 85.7 | 85.4 | 85.1 | 84.7 | 84.4 |
| Croscarmellose Sodium | 12.9 | 12.8 | 12.8 | 12.7 | 12.7 |
| Colloidal Silica | 0.5 | 0.9 | 1.2 | 1.7 | 2.1 |
| Stearic Acid | 0.9 | 0.9 | 0.9 | 0.9 | 0.8 |

Examples 13-17 were prepared in the same manner as described in Example 1 to produce tablets containing 200 mg ibuprofen. The dissolution results are given Tables 4 (pH 7.2) and 5 (pH 5.8) below.

TABLE 4

Dissolution Results at pH 7.2

| Time (min) | Ex 13 | Ex 14 | Ex 15 | Ex 16 | Ex 17 |
| --- | --- | --- | --- | --- | --- |
| 0 | 0.0% | 0.0% | 0.0% | 0.0% | 0.0% |
| 5 | 77.1% | 66.3% | 69.6% | 73.2% | 89.4% |
| 10 | 87.3% | 82.0% | 85.9% | 86.6% | 98.1% |
| 20 | 96.8% | 98.4% | 99.1% | 98.6% | >100% |
| 30 | 98.2% | 99.6% | 99.6% | 99.3% | >100% |
| 45 | 98.3% | 99.6% | 99.6% | 99.4% | >100% |
| 60 | 98.3% | 99.7% | 99.6% | 99.4% | >100% |

TABLE 5

| | | Dissolution Results at pH 5.8 | | | |
|---|---|---|---|---|---|
| Time (min) | Ex 13 | Ex 14 | Ex 15 | Ex 16 | Ex 17 |
| 0 | 0.0% | 0.0% | 0.0% | 0.0% | 0.0% |
| 5 | 30.4% | 28.5% | 24.1% | 29.1% | 35.3% |
| 10 | 51.2% | 47.0% | 43.0% | 48.0% | 56.3% |
| 20 | 69.9% | 64.3% | 63.7% | 66.0% | 71.4% |
| 30 | 77.6% | 72.8% | 75.8% | 79.0% | 75.9% |
| 45 | 83.7% | 85.0% | 90.3% | 91.3% | 78.4% |
| 60 | 88.0% | 93.2% | 95.5% | 96.3% | 80.0% |

EXAMPLES 8-21

| | Ex 18 (% w/w) | Ex 19 (% w/w) | Ex 20 (% w/w) | Ex 21 (% w/w) |
|---|---|---|---|---|
| Granular component: | | | | |
| Ibuprofen | 79.0 | 84.1 | 84.0 | 85.7 |
| Croscarmellose Sodium | 11.9 | 12.6 | 12.6 | 12.9 |
| Poloxamer | 7.9 | 2.1 | — | — |
| Sodium Lauryl Sulphate | — | — | 2.2 | 0.2 |
| Extra-granular component: | | | | |
| Colloidal Silica | 0.4 | 0.4 | 0.4 | 0.4 |
| Stearic Acid | 0.8 | 0.8 | 0.8 | 0.8 |

Examples 18-21 were prepared in the same manner as described in Example 1, except that a surfactant (Poloxamer/sodium lauryl sulphate) was dispersed within the molten ibuprofen after the croscarmellose sodium had been dispersed uniformly within the molten ibuprofen. Tablets containing 200 mg ibuprofen were prepared.

The dissolution results for the tablets of Examples 18 to 21 at pH 7.2 and 5.8 are given in Table 6 (a) and (b) below.

TABLE 6(a)

| | Dissolution Results | | | |
|---|---|---|---|---|
| | Example 18 | | Example 19 | |
| Time (min) | pH 7.2 | pH 5.8 | pH 7.2 | pH 5.8 |
| 0 | 0.0% | 0.0% | 0.0% | 0.0% |
| 5 | 38.5% | 24.0% | 44.6% | 26.0% |
| 10 | 79.2% | 59.1% | 95.5% | 73.7% |
| 20 | 96.2% | 91.3% | 99.5% | 95.2% |
| 30 | 96.4% | 98.0% | 99.6% | >100% |
| 45 | 96.4% | >100% | 99.6% | >100% |
| 60 | 96.4% | >100% | 99.6% | >100% |

TABLE 6(b)

| | Dissolution Results | | | |
|---|---|---|---|---|
| | Example 20 | | Example 21 | |
| Time (min) | pH 7.2 | pH 5.8 | pH 7.2 | pH 5.8 |
| 0 | 0.0% | 0.0% | 0.0% | 0.0% |
| 5 | 31.9% | 19.1% | 90.1% | 54.8% |
| 10 | 73.7% | 57.8% | 96.6% | 76.9% |
| 20 | 95.9% | 90.4% | 97.0% | 89.8% |
| 30 | 97.4% | 96.6% | 97.2% | 94.0% |
| 45 | 97.5% | 98.1% | 97.3% | 96.3% |
| 60 | 97.5% | 98.1% | 97.3% | 97.2% |

EXAMPLES 22-26

| | Ex22 (% w/w) | Ex 23 (% w/w) | Ex 24 (% w/w) | Ex 25 (% w/w) | Ex 26 (% w/w) |
|---|---|---|---|---|---|
| Granular Composition: | | | | | |
| Ibuprofen | 82.4 | 82.4 | 79.0 | 82.4 | 70.6 |
| Croscarmellose sodium | 12.3 | 12.3 | 11.9 | 12.3 | 10.6 |
| Extra-granular Component: | | | | | |
| Microcrystalline cellulose | 4.1 | — | — | — | 17.6 |
| Lactose | — | 4.1 | 7.9 | — | — |
| Dicalcium phosphate | — | — | — | 4.1 | — |
| Colloidal silicon dioxide | 0.4 | 0.4 | 0.4 | 0.4 | 0.4 |
| Stearic acid | 0.8 | 0.8 | 0.8 | 0.8 | 0.8 |

Examples 22-26 were prepared in the same manner as described in Example 1, except that a diluent (microcrystalline cellulose/lactose/dicalcium phosphate) was included in the extra-granular component. Tablets containing 200 mg ibuprofen were prepared.

The dissolution results for each Example at pH 7.2 are given in Table 7 below.

TABLE 7

Dissolution Results at pH 7.2

| Time (min) | Ex 22 | Ex 23 | Ex 24 | Ex 25 | Ex 26 |
|---|---|---|---|---|---|
| 0 | 0.0% | 0.0% | 0.0% | 0.0% | 0.0% |
| 5 | 78.8% | 71.5% | 85.2% | 79.0% | 84.1% |
| 10 | 87.7% | 82.9% | 94.3% | 87.3% | 95.6% |
| 20 | 95.4% | 91.2% | 98.2% | 93.9% | >100% |
| 30 | 100.0% | 94.6% | 98.6% | 96.6% | >100% |
| 45 | >100% | 95.1% | 98.7% | 96.7% | >100% |
| 60 | >100% | 95.1% | 98.7% | 96.7% | >100% |

EXAMPLES 27-28

|  | Ex 27 (% w/w) | Ex 28 (% w/w) |
|---|---|---|
| Granular Component: |  |  |
| Ibuprofen | 79.0 | 70.6 |
| Croscarmellose sodium | 11.9 | 10.6 |
| Microcrystalline cellulose | 7.9 | — |
| Dicalcium phosphate | — | 17.6 |
| Extra-granular component: |  |  |
| Colloidal silicon dioxide | 0.4 | 0.4 |
| Stearic acid | 0.8 | 0.8 |

Examples 27 and 28 were prepared in the same manner as described in Example 1, except that a diluent (microcrystalline cellulose/dicalcium phosphate) was dispersed within the molten ibuprofen after the croscarmellose sodium had been dispersed uniformly within the molten ibuprofen. Tablets containing 200 mg ibuprofen were prepared. The dissolution results at pH 7.2 are given in Table 8 below

EXAMPLES 29-30

|  | Ex 29 (% w/w) | Ex 30 (% w/w) |
|---|---|---|
| Granular Component: |  |  |
| Ibuprofen | 70.6 | 79.1 |
| Croscarmellose sodium | 10.6 | 11.9 |
| Lactose | 8.8 | — |
| Dicalcium phosphate | — | 3.9 |
| Extra-granular component: |  |  |
| Colloidal silicon dioxide | 0.4 | 0.4 |
| Stearic acid | 0.8 | 0.8 |
| Lactose | 8.8 | — |
| Dicalcium phosphate | — | 3.9 |

Examples 29 and 30 were prepared in the same manner as described in Example 1, except that a half portion of a diluent (lactose/dicalcium phosphate) was dispersed within the molten ibuprofen after the disintegrant had been uniformly dispersed within the molten ibuprofen and the remaining half portion of diluent was included in the extra-granular component. Tablets containing 200 mg ibuprofen were prepared. The dissolution results for each Example at pH 7.2 are given in Table 8 below.

TABLE 8

Dissolution Results at pH 7.2

| Time (min) | Ex 27 | Ex 28 | Ex 29 | Ex 30 |
|---|---|---|---|---|
| 0 | 0.0% | 0.0% | 0.0% | 0.0% |
| 5 | 87.7% | 50.6% | 82.5% | 82.8% |
| 10 | 95.3% | 59.5% | 93.0% | 90.1% |
| 20 | 98.4% | 67.0% | 95.8% | 92.3% |
| 30 | 98.8% | 71.3% | 95.7% | 93.0% |
| 45 | 98.9% | 75.6% | 95.7% | 93.7% |
| 60 | 98.9% | 78.8% | 95.7% | 94.1% |

EXAMPLE 31

|  | Ex 31 (% w/w) |
|---|---|
| Flurbiprofen | 21.7 |
| Croscarmellose sodium | 3.3 |
| Colloidal silicon dioxide | 0.1 |
| Stearic acid | 0.2 |
| Microcrystalline cellulose | 74.7 |

Example 31 was prepared in the same manner as described in Example 1 except that flurbiprofen was used as the NSAID and microcrystalline cellulose was included in the extra-granular component i.e. with colloidal silicon dioxide and stearic acid. Tablets containing 50 mg flurbiprofen were prepared. The dissolution results at pH 7.2 are given in Table 9 below.

TABLE 9

Dissolution Results at pH 7.2

| Time (min) | Ex 31 |
|---|---|
| 0 | 0.0% |
| 5 | 82.8% |
| 10 | 85.6% |
| 20 | 86.0% |
| 30 | 86.1% |
| 45 | 86.2% |
| 60 | 86.3% |

EXAMPLES 32-34

|  | Ex 32 (% w/w) | Ex 33 (% w/w) | Ex 34 (% w/w) |
|---|---|---|---|
| Ibuprofen | 82.3 | 79.0 | 76.0 |
| Croscarmellose sodium | 16.5 | 19.8 | 22.8 |
| Colloidal silicon dioxide | 0.4 | 0.4 | 0.4 |
| Stearic acid | 0.8 | 0.8 | 0.8 |

Examples 32-34 were prepared in the same way as described in Example 1 to provide tablets containing 200 mg ibuprofen. The dissolution results are given in Tables 10 (pH 7.2) and 11 (pH 5.8) below.

TABLE 10

Dissolution Results at pH 7.2

| Time (min) | Ex 32 | Ex 33 | Ex 34 |
|---|---|---|---|
| 0 | 0.0% | 0.0% | 0.0% |
| 5 | 58.0% | 70.9% | 39.7% |
| 10 | 76.9% | 82.2% | 60.9% |
| 20 | 89.6% | 92.3% | 80.8% |
| 30 | 96.8% | 95.9% | 90.9% |
| 45 | 98.5% | 97.2% | 97.1% |
| 60 | 98.6% | 97.2% | 97.3% |

TABLE 11

Dissolution Results at pH 5.8

| Time (min) | Ex 32 | Ex 33 | Ex 34 |
|---|---|---|---|
| 0 | 0.0% | 0.0% | 0.0% |
| 5 | 34.7% | 37.9% | 23.1% |
| 10 | 62.1% | 68.7% | 47.3% |
| 20 | 87.1% | 90.6% | 70.8% |
| 30 | 95.7% | 97.3% | 85.7% |
| 45 | 99.0% | 99.2% | 93.1% |
| 60 | 99.7% | 99.0% | 94.3% |

EXAMPLES 35-38

|  | Ex 35 (% w/w) | Ex 36 (% w/w) | Ex 37 (% w/w) | Ex 38 (% w/w) |
|---|---|---|---|---|
| Granular Component: | | | | |
| Ibuprofen | 85.6 | 85.1 | 84.8 | 84.4 |
| Croscarmellose sodium | 12.8 | 12.8 | 12.8 | 12.8 |
| Colloidal silicon dioxide | 0.8 | 1.3 | 1.6 | 2.0 |
| Extra-granular component: | | | | |
| Stearic acid | 0.8 | 0.8 | 0.8 | 0.8 |

Examples 35-38 were prepared in the same way as described in Example 1 except that the colloidal silicon dioxide was dispersed uniformly within the molten ibuprofen before the disintegrant was uniformly dispersed within the molten ibuprofen. Tablets containing 200 mg ibuprofen were produced. The dissolution results are given in Table 12 below.

TABLE 12

Dissolution Results at pH 7.2

| Time (min) | Ex 35 | Ex 36 | Ex 37 | Ex 38 |
|---|---|---|---|---|
| 0 | 0.0% | 0.0% | 0.0% | 0.0% |
| 5 | 72.7% | 64.8% | 72.7% | 78.1% |
| 10 | 85.0% | 75.8% | 90.1% | 89.4% |
| 20 | 92.8% | 84.5% | 96.1% | 95.2% |
| 30 | 97.8% | 95.2% | 97.4% | 98.1% |
| 45 | 98.3% | 99.0% | 98.4% | 98.2% |
| 60 | 98.5% | 99.5% | 98.4% | 98.2% |

EXAMPLES 39-42

|  | Ex 39 (% w/w) | Ex 40 (% w/w) | Ex 41 (% w/w) | Ex 42 (% w/w) |
|---|---|---|---|---|
| Granular component: | | | | |
| Ibuprofen | 85.82 | 85.6 | 85.5 | 82.3 |
| Croscarmellose Sodium | 12.86 | 12.9 | 12.8 | 12.3 |
| Sodium lauryl sulphate | 0.04 | 0.2 | 0.4 | 4.1 |
| Extra-granular component: | | | | |
| Colloidal Silica | 0.43 | 0.4 | 0.4 | 0.4 |
| Stearic Acid | 0.85 | 0.9 | 0.9 | 0.9 |

Examples 39-42 were prepared in the same way as described in Example 1 except that sodium lauryl sulphate was dispersed uniformly within the molten ibuprofen after the disintegrant had been uniformly dispersed within the ibuprofen melt. Tablets containing 200 mg ibuprofen were produced. The dissolution results are given in Table 13 below.

TABLE 13

Dissolution Results at pH 7.2

| Time (min) | Ex 39 | Ex 40 | Ex 41 | Ex 42 |
|---|---|---|---|---|
| 0 | 0.0% | 0.0% | 0.0% | 0.0% |
| 5 | 95.7% | 76.0% | 62.7% | 24.0% |
| 10 | >100% | 95.9% | 81.8% | 50.0% |
| 20 | >100% | 98.7% | 97.3% | 74.4% |
| 30 | >100% | 98.8% | 99.2% | 89.4% |
| 45 | >100% | 98.8% | 99.2% | >100% |
| 60 | >100% | 98.8% | 99.2% | >100% |

EXAMPLE 43

|  | (% w/w) |
|---|---|
| Granular Component: | |
| Ibuprofen | 82.6 |
| Croscarmellose sodium | 12.4 |
| Hydrogenated Castor Oil | 2.1 |
| Extra-granular component: | |
| Colloidal silicon dioxide | 2.1 |
| Stearic acid | 0.8 |

Example 43 was prepared in the same way as described in Example 1 except that hydrogenated castor oil was dispersed uniformly within the molten ibuprofen after the disintegrant had been uniformly dispersed within the ibuprofen melt. Tablets containing 200 mg ibuprofen were produced. The dissolution results are given in Table 14 below.

TABLE 14

Dissolution Results at pH 7.2

| Time (min) | |
|---|---|
| 0 | 0.0% |
| 5 | 76.6% |
| 10 | 98.7% |

TABLE 14-continued

Dissolution Results at pH 7.2

| Time (min) | |
| --- | --- |
| 20 | 99.1% |
| 30 | 99.1% |
| 45 | 99.1% |
| 60 | 99.1% |

EXAMPLES 44-45

| | Ex 44 (% w/w) | Ex 45 (% w/w) |
| --- | --- | --- |
| Granular component: | | |
| Ibuprofen | 79.1 | 72.2 |
| Croscarmellose sodium | 11.9 | 10.8 |
| Tripotassium citrate monohydrate | 7.7 | — |
| Sodium citrate | — | 15.7 |
| Sodium lauryl sulphate | 0.2 | 0.2 |
| Extra-granular component: | | |
| Colloidal silica | 0.4 | 0.4 |
| Stearic acid | 0.7 | 0.7 |

Examples 44 and 45 were prepared in the same way as described in Example 39 except that firstly, the disintegrant was dispersed uniformly within the molten ibuprofen; secondly, the diluent (tripotassium citrate monohydrate/sodium citrate) was dispersed uniformly therethrough and finally the sodium lauryl sulphate was dispersed within the molten ibuprofen. Tablets containing 200 mg ibuprofen were produced. The dissolution results are given in Table 15 below.

TABLE 15

| | Dissolution Results | | | |
| --- | --- | --- | --- | --- |
| | Ex 44 | | Ex 45 | |
| TIME (min) | pH 7.2 | pH 6.0 | pH 7.2 | pH 6.0 |
| 0 | 0.0% | 0.0% | 0.0% | 0.0% |
| 5 | 49.4% | 40.6% | 59.8% | 47.8% |
| 10 | 94.7% | 80.7% | 95.2% | 85.9% |
| 20 | 99.5% | 93.2% | 97.4% | 97.6% |
| 30 | 99.5% | 96.2% | 97.4% | 98.4% |
| 45 | 99.5% | 97.2% | 97.4% | 98.0% |
| 60 | 99.5% | 97.2% | 97.4% | 97.8% |

EXAMPLE 46

| | (% w/w) |
| --- | --- |
| Granular Component: | |
| Ibuprofen | 86.3 |
| Croscarmellose Sodium | 12.9 |
| Sodium lauryl sulphate | 0.2 |
| Extra-granular component: | |
| Colloidal Silica | 0.4 |
| Sodium lauryl sulphate | 0.2 |

Example 46 was prepared in the same way as described in Example 39 except that sodium lauryl sulphate was also incorporated in the extra-granular component as well as in the granular component. Tablets containing 200 mg ibuprofen were produced.

EXAMPLE 47

| | (% w/w) |
| --- | --- |
| Granular Component: | |
| Ibuprofen | 31.5 |
| Croscarmellose Sodium | 4.7 |
| Sugar | 31.5 |
| Sodium bicarbonate | 12.8 |
| Extra-granular component: | |
| Colloidal Silica | 0.2 |
| Stearic Acid | 0.3 |
| Citric Acid Monohydrate | 1.6 |
| Sorbitol | 15.7 |
| Flavouring/Sweeteners | 1.7 |

A dispersible tablet adapted to be dispersed in water prior to ingestion was prepared in a similar manner to that described in Example 1, incorporating sugar and sodium bicarbonate into the melt granule and citric acid, sorbitol powder, flavourings and sweeteners in the basing ingredients. Tablets containing 200 mg ibuprofen were prepared.

EXAMPLE 48

A composition containing the following ingredients was prepared according to the processes outlined below:

| | Ex 48 (% w/w) |
| --- | --- |
| Granular Composition: | |
| Ibuprofen | 85.8 |
| Croscarmellose Sodium | 12.9 |
| Basing ingredients: | |
| Colloidal Silica | 0.4 |
| Stearic Acid | 0.9 |

EXAMPLE 48a

The ibuprofen was added to a steam-jacketed vessel and heated to 75-80° C. until the ibuprofen was fully molten. The croscarmellose sodium was added to the molten ibuprofen and stirred to maintain a suspension of the croscarmellose sodium in the molten ibuprofen. The mixture was discharged onto a stainless steel tray and allowed to cool. After the entire mass had solidified, it was passed through a cone mill having a screen with a round hole size of 1 mm. A granulate having a median particle size in the range 150-250 μm was collected.

The colloidal silicon dioxide and stearic acid were added to the granulate and blended until a uniform mixture was formed. The blended mixture was compressed into tablets on a conventional tabletting machine to form tablets containing 200 mg ibuprofen. Optionally, the tablets may be coated with a conventional sugar or film coat.

It was found that the tablets produced had the following characteristics:

| | |
|---|---|
| Tablet Crushing Strength: | 30-80 N |
| Tablet Friability: | No tablets capped or broken after 10 minutes Weight loss <0.1% |

EXAMPLE 48b

The following Example describes a one step process involving melting, cooling and granulation within the same vessel (as described above) to produce the melt granulation. The equipment comprises a jacketed vessel which allowed steam heating/water cooling, fitted with both a low speed stirrer and a high-speed cutter/granulator. Equipment of this type is available from Niro/Fielder Limited. Another example would be of a Colette mixer.

The ibuprofen and croscarmellose sodium were added as dry powders to the jacketed vessel. They were heated to 75° C. with stirring until the ibuprofen was fully molten and the croscarmellose sodium maintained as a suspension in the liquid ibuprofen. At this stage, the steam heating was stopped and the vessel cooled by circulating cold water within the jacket. As the mixture cooled, it becomes more viscous. A high speed rotary cutter was set in motion to break down the solidifying mass into a granulate. The granulate was further milled to produce a granulate having a mean particle size of in the range 150-250 μm.

The colloidal silicon dioxide and stearic acid were added to the granulate and blended until a uniform mixture was formed. The blended mixture was compressed into tablets containing 200 mg ibuprofen. Optionally, the tablets may be coated with a conventional sugar or film coat.

It was found that the tablets produced had the following characteristics:

| | |
|---|---|
| Tablet Crushing Strength: | 30-80 N |
| Tablet Friability: | No tablets capped or broken after 10 minutes Weight loss <0.1% |

EXAMPLE 48c

The following Example describes the production of the melt granulation by spray granulation. In this process the ingredients were melted in a suitable vessel and pumped to the spray head of a spray granulator. The melt was sprayed into the flow of cold air and the resultant granulate formed by the agglomeration of melt onto solidified particles.

The ibuprofen and croscarmellose sodium were added as dry powders to the jacketed vessel. They were heated to 75° C. with stirring until the ibuprofen was fully molten and the croscarmellose sodium maintained as a suspension in the liquid ibuprofen.

The mixture was transferred to a spray granulator via a trace-heated line. The melt dispersion was sprayed into a stream of cold air, controlling the spray rate of feed material and the rate of removal of the particles, until suitably sized particles for tabletting were formed. The granulate was discharged into a container.

The colloidal silicon dioxide and stearic acid were added to the granulate and blended until a uniform mixture was formed. The blended mixture was compressed into tablets containing 200 mg ibuprofen. Optionally, the tablets may be coated with a sugar or film coat.

It was found that the tablets produced had the following characteristics:

| | |
|---|---|
| Tablet Crushing Strength: | 30-80 N |
| Tablet Friability: | No tablets capped or broken after 10 minutes Weight loss <0.1% |

EXAMPLE 48d

The melt formulation was produced using a spray tower drier. This process is similar to the spray granulation process but differed in that the granulate was formed from a spray dispersion in one step.

The ibuprofen and croscarmellose sodium were added as dry powders to the jacketed vessel. They were heated to 75° C. with stirring until the ibuprofen was fully molten and the croscarmellose sodium maintained as a suspension in the liquid ibuprofen.

The mixture was transferred to the spray head, situated at the top of a spray tower via trace-heated line. The melt dispersion was sprayed into a stream of cold air until particles were formed directly by solidification of the melt onto solid particles. The cooled solidified granulate was collected and placed in a container.

The colloidal silicon dioxide and stearic acid were added to the granulate and blended until a uniform mixture was formed. The blended mixture was compressed into tablets containing 200 mg ibuprofen. Optionally, the tablets may be coated with a conventional sugar or film coat.

It was found that the tablets produced had the following characteristics:

| | |
|---|---|
| Tablet Crushing Strength: | 30-80 N |
| Tablet Friability: | No tablets capped or broken after 10 minutes Weight loss <0.1% |

EXAMPLE 48e

The ibuprofen and croscarmellose sodium were blended to form a uniform powder mixture which was then introduced into the heated chamber of a twin screw extruder via a screw-feed hopper system. The extruder barrel was heated to a temperature given below. The ingredients were heated and worked in the extruder until the ibuprofen was fully molten. A continuous molten ribbon of extrudate was discharged onto a cooled stainless steel band to allow the extrudate to cool over a period of up to 1 minute. The solidified mass was broken and passed through a cone mill having a screen with a round hole size of 1 mm to produce a granulate having a median particle size in the range 150-250 μm, blended with colloidal silicon dioxide and stearic acid until a uniform mixture was produced. The mixture was compressed to produce tablets containing 200 mg ibuprofen. An optional sugar or film coating using conventional process technology may be applied to the tablets.

The following extruders were tried:

|   | Extruder Model | L/D ratio* | Temperature of barrel | Output |
|---|---|---|---|---|
| 1 | MP 19 | 40:1 | 17° C. | 10 kg/hr |
| 2 | MP 19 | 25:1 | 80° C. | 10 kg/hr |
| 3 | MP 19 | 17.5:1 | 80° C. | 10 kg/hr |
| 4 | MP 40PC | 17.5:1 | 90° C. | 100 kg/hr |

*L/D ratio = length:diameter

It was found that the tablets produced had the following characteristics:

| | |
|---|---|
| Tablet Crushing Strength: | 30-80 N |
| Tablet Friability: | No tablets capped or broken after 10 minutes Weight loss < 0.1% |
| Dissolution Results | See Table 16 below |

(MP 19 Extruder; L/D ratio 17.5:1)

TABLE 16

| Dissolution Results at pH 7.2 | |
|---|---|
| Time (min) | |
| 0 | 0.0% |
| 5 | 82.4% |
| 10 | 96.9% |
| 20 | 98.9% |
| 30 | 99.1% |
| 45 | 99.2% |
| 60 | 99.2% |

In the same way, tablets containing 50 mg, 100 mg, 150 mg, 200 mg, 300 mg and 400 mg ibuprofen, S(+)-ibuprofen, flurbiprofen, S(+)-flurbiprofen, ketoprofen, S(+)-ketoprofen, naproxen and S(+)-naproxen can be prepared. Optionally, an inert diluent such as a conventional sugar and/or cellulose material may also be incorporated to account for the difference in dosages required to achieve a therapeutic effect in comparison to the amount of ibuprofen normally incorporated into solid dosage forms.

Furthermore, the following disintegrants may replace the disintegrants illustrated herein in each of the illustrative Examples:

wheat starch, maize starch, potato starch, low-substituted hydroxypropyl cellulose, algnic acid, cross-linked polyvinyl pyrrolidone and magnesium aluminium silicate.

For example, there may also be prepared the following Examples in a similar manner to be illustrative Examples previously described:

EXAMPLES 49-55

| | Ex 49 (% w/w) | Ex 50 (% w/w) | Ex 51 (% w/w) |
|---|---|---|---|
| Granular component: | | | |
| Ibuprofen | 67.6 | 65.3 | 63.3 |
| Croscarmellose Sodium | 3.4 | 6.5 | 9.5 |
| Extra-granular component: | | | |
| Colloidal Silica | 1.0 | 1.0 | 1.0 |
| Stearic Acid | 0.7 | 0.7 | 0.7 |
| Sodium Bicarbonate | 27.3 | 26.5 | 25.5 |

| | Ex 52 (% w/w) | Ex 53 (% w/w) | Ex 54 (% w/w) | Ex 55 (% w/w) |
|---|---|---|---|---|
| Granular component: | | | | |
| Ibuprofen | 82.3 | 82.3 | 82.3 | 82.3 |
| Croscarmellose Sodium | 16.3 | 12.4 | 12.4 | 12.2 |
| Sodium Citrate | — | 4.1 | — | 4.1 |
| Potassium Citrate | — | — | 4.1 | — |
| Sodium Lauryl Sulphate | 0.2 | — | — | 0.2 |
| Extra-granular component: | | | | |
| Colloidal Silicon Dioxide | 0.4 | 0.4 | 0.4 | 0.4 |
| Stearic Acid | 0.8 | 0.8 | 0.8 | 0.8 |
| Sodium Lauryl Sulphate | — | — | — | — |

EXAMPLES 56-61

| | Ex 56 (% w/w) | Ex 57 (% w/w) | Ex 58 (% w/w) |
|---|---|---|---|
| Granular component: | | | |
| Ibuprofen | 79.0 | 79.0 | 82.3 |
| Croscarmellose Sodium | 11.9 | 11.9 | 12.2 |
| Sodium Citrate | 7.9 | — | — |
| Potassium Citrate | — | 7.9 | 4.1 |
| Sodium Lauryl Sulphate | — | — | 0.2 |
| Extra-granular component: | | | |
| Colloidal Silicon Dioxide | 0.4 | 0.4 | 0.8 |
| Stearic Acid | 0.8 | 0.8 | — |
| Sodium Lauryl Sulphate | — | — | 0.2 |

| | Ex 59 (% w/w) | Ex 60 (% w/w) | Ex 61 (% w/w) |
|---|---|---|---|
| Granular component: | | | |
| Ketoprofen (50 mg/tablet) | 31.3 | 45.5 | — |
| Naproxen (250 mg/tablet) | — | — | 88.3 |
| Croscarmellose Sodium | 5.0 | 7.2 | 10.6 |
| Extra-granular component: | | | |
| Colloidal Silica | 0.6 | 0.9 | 0.4 |
| Stearic Acid | 0.6 | 0.9 | 0.7 |
| Microcrystalline cellulose | 62.5 | 45.5 | — |

EXAMPLES 62-64

| | Ex 62 (% w/w) | Ex 63 (% w/w) | Ex 64 (% w/w) |
|---|---|---|---|
| Granular component: | | | |
| Ibuprofen | 79.1 | 79.1 | 72.2 |
| Croscarmellose sodium | 11.9 | 19.5 | 11.0 |
| Sodium citrate | 7.6 | — | 15.7 |
| Sodium lauryl sulphate | 0.2 | 0.2 | — |
| Extra-granular component: | | | |
| Colloidal silicon dioxide | 0.4 | 0.4 | 0.4 |
| Stearic acid | 0.8 | 0.8 | 0.7 |

COMPARATIVE EXAMPLES

Comparative Example 1

Compressed Tablets Without Silicon Dioxide

The granular component for the comparative Examples was produced in a similar manner to that described for the illustrative Examples. The granular component of comparative Examples A-D contained only melt granules of ibuprofen together with different amounts of croscarmellose sodium as disintegrating agent. Tablets were formed by compressing the granular component without any extra-granular component. The granular component of comparative Examples E-H contained ibuprofen and croscarmellose sodium in different proportions. The granular component was combined with 1% stearic acid as the only ingredient in the extra-granular component.

Comparative Example 1

| Example | Dissolution time | | | | |
|---|---|---|---|---|---|
| | 10 mins | 20 mins | 30 mins | 45 mins | 60 mins |
| A (5% disintegrating agent) | 2.6% | 5.7% | 9.6% | 14.3% | 18.8% |
| B (8% disintegrating agent) | 2.2% | 7.3% | 10.1% | 15.5% | 19.9% |
| C (10% disintegrating agent) | 0.1% | 0.0% | −0.1% | 0.0% | 0.0% |
| D (15% disintegrating agent) | −0.9% | 3.4% | 6.7% | 10.8% | 15.8% |
| E (5% disintegrating agent) | 1.2% | 5.5% | 8.8% | 13.2% | 17.9% |
| F (8% disintegrating agent) | 0.4% | 5.8% | 8.6% | 13.5% | 16.6% |
| G (10% disintegrating agent) | 2.4% | 5.9% | 9.7% | 15.5% | 20.4% |
| H (15% disintegrating agent) | 1.3% | 5.4% | 9.8% | 14.2% | 20.7% |

It can be seen that the above comparative Example gives relatively poor dissolution compared with the illustrative Examples according to the present invention.

Comparative Example 2

The following Example is taken from Japanese Patent Application 120616 (1981) (Example 5). This example prepares tablets containing 200 mg ibuprofen containing the ingredients listed below.

| | % w/w |
|---|---|
| Ibuprofen | 79.4 |
| Microcrystalline cellulose | 7.9 |
| Hydroxypropyl starch | 11.9 |
| Calcium stearate | 0.8 |

The dissolution results at pH 7.2 are provided in Comparative Table 2 below.

COMPARATIVE TABLE 2
Dissolution Results at pH 7.2

| Time (min) | |
|---|---|
| 0 | 0.0% |
| 5 | 13.1% |
| 10 | 23.4% |
| 20 | 35.7% |
| 30 | 43.5% |
| 45 | 51.8% |
| 60 | 58.0% |

It can be seen that the above comparative Example gives relatively poor dissolution compared with the illustrative Examples according to the present invention.

Comparative Example 3

The Example 48 formulation was processed through the MP 19 extruder (L/D ratio 17.5:1) in which the barrel was heated to 75° C. (Test A) or 50° C. (Test B). The Ibuprofen in Test A fully melted. However, in Test B, a significant amount of the Ibuprofen did not melt and thus the ibuprofen was present as two phases. The dissolution results, at pH 5.8 for Test A and Test B are given below in Comparative Table 3.

COMPARATIVE TABLE 3
Dissolution Results at pH 5.8

| Time (min) | Test A | Test B |
|---|---|---|
| 0 | 0.0% | 0.0% |
| 5 | 41.6% | 23.9% |
| 10 | 66.7% | 45.3% |
| 20 | 85.4% | 71.3% |
| 30 | 92.4% | 85.5% |
| 45 | 96.2% | 94.0% |
| 60 | 97.5% | 96.6% |

It can be seen that the dissolution results for the comparative Example (Test B) are significantly poorer that the dissolution results for a composition according to present invention (Test A).

The invention claim is:

1. A compressed tablet composition comprising:
    a granular component comprising a plurality of solidified melt granules of a non-steroidal anti-inflammatory drug having a melting point in the range of 30-300° C., wherein a disintegrant is uniformly dispersed therein;
    wherein all of the non-steroidal anti-inflammatory drug within the granules is present as a single continuous crystalline phase, wherein the tablet composition comprises silicon dioxide present in an amount of 0.05-5.0% by weight of the composition, and wherein the non-steroidal anti-inflammatory drug is 60-97% by weight of the tablet composition.

2. The compressed tablet composition according to claim 1 wherein the silicon dioxide is present as an extra-granular component.

3. The compressed tablet composition according to claim 2 wherein the extra-granular component further comprises a lubricant.

4. The compressed tablet composition according to claim 1 wherein the granular component further comprises a surfactant.

5. The compressed tablet composition according to claim 2 wherein
   a) said granular component is 60-99.95% by weight of the composition, and said disintegrant is 0.05-1 parts by weight per part by weight of non-steroidal anti-inflammatory drug;
   b) said extra-granular component is 0.05-40% by weight of the composition.

6. The compressed tablet composition according to claim 1, wherein the non-steroidal anti-inflammatory drug is selected from the group consisting of ibuprofen, flurbiprofen, ketoprofen, naproxen and enantiomers thereof.

7. The compressed tablet composition according to claim 1, wherein the non-steroidal anti-inflammatory drug is an ibuprofen medicament.

8. The compressed tablet composition according to claim 1, wherein the disintegrant is selected from the group consisting of sodium starch glycolate and croscarmellose sodium.

9. The compressed tablet composition according to claim 1, wherein said silicon dioxide is present at 0.1-3% by weight of the composition.

10. The compressed tablet composition according to claim 1, further comprising diluent which is present at 0.1-20% by weight of the composition.

11. The compressed tablet composition according to claim 1, wherein the granular component comprises 70-95% non-steroidal anti-inflammatory drug by weight of the granular component.

12. The compressed tablet composition according to claim 7, wherein the composition comprises
   a) 90-99.95% granular component by weight of the composition, said granular component comprising solidified melt granules of ibuprofen incorporating croscarmellose sodium uniformly dispersed therein, said ibuprofen being present in an amount of 70-99% by weight of the composition, said croscarmellose sodium being present in an amount of 1-25% by weight of the composition, and further comprising
   b) 0.05-10% extra-granular component by weight of the composition, wherein said extra-granular component comprises:
      (i) 0.1-3% lubricant by weight of the composition; and
      (ii) 0.05-2% silicon dioxide by weight of the composition.

13. The compressed tablet composition according to claim 12, wherein the solidified melt granules further comprise a diluent uniformly dispersed therein, and the diluent is present in an amount of up to 20% by weight of the composition.

14. The compressed tablet composition according to claim 13, wherein the granular component consists essentially of ibuprofen, croscarmellose sodium and a diluent selected from the group consisting of microcrystalline cellulose and a salt of an organic acid.

15. The compressed tablet composition according to claim 1, wherein said non-steroidal anti-inflammatory drug is ibuprofen in an amount of 70-95% by weight of the composition.

16. The compressed tablet composition according to claim 1, wherein said disintegrant is croscarmellose sodium in an amount of 3-20% by weight of the composition.

17. The compressed tablet composition according to claim 3, wherein said extra-granular component consists essentially of silicon dioxide and a lubricant in a ratio of 1 part by weight silicon dioxide to 0.05-5 parts by weight lubricant.

18. The compressed tablet composition according to claim 10, wherein
   a) said granular component comprises:
      (i) 70-90% ibuprofen by weight of the composition;
      (ii) 8-20% croscarmellose sodium by weight of the composition;
      (iii) 0-20% diluent by weight of the composition; and further comprising
   b) an extra-granular component comprising:
      (iv) 0.5-2% stearic acid or a salt thereof by weight of the composition;
      (v) 0.1-2.5% silicon dioxide by weight of the composition,
   wherein the sum of components (i) to (v) being greater than 99% by weight of the composition.

19. A method for improving the dissolution of a nonsteroidal anti-inflammatory drug from a compressed composition under aqueous conditions, comprising forming a compressed composition by combining a granular component with an extra-granular silicon dioxide component, said granular component comprising a plurality of solidified melt granules of a non-steroidal anti-inflammatory drug having a melting point in the range of 30-300° C. and incorporating a disintegrant uniformly dispersed therein, wherein said silicon dioxide is present in an amount of 0.05-5% by weight, wherein all of the non-steroidal anti-inflammatory drug within the granules is present as a single continuous crystalline phase, and wherein the non-steroidal anti-inflammatory drug is 60-97% by weight of the composition.

20. The method according to claim 19, wherein the solidified melt granules further comprise a diluent uniformly dispersed therein.

21. A process for preparing a compressed tablet composition, comprising:
   a) combining a non-steroidal anti-inflammatory drug in fully molten form with a disintegrant, to form a uniform mixture;
   b) cooling said mixture to form a solidified melt;
   c) forming said solidified melt into granules;
   d) compressing said granules, to form a compressed tablet composition;
   wherein the tablet composition comprises a granular component comprising a plurality of solidified melt granules of a non-steroidal anti-inflammatory drug having a melting point in the range of 30-300° C., wherein a disintegrant is uniformly dispersed therein;
   wherein the non-steroidal anti-inflammatory drug within the melt granules is present as a continuous phase, wherein the tablet composition comprises silicon dioxide present in an amount of 0.05 to 5% by weight of the composition, and wherein the non-steroidal anti-inflammatory drug is 60-97% by weight of the tablet composition.

22. The method according to claim 21, further comprising an extra-granular component.

23. The process according to claim 21, wherein the silicon dioxide is present as an extra-granular component.

24. The process according to claim 21, wherein said non-steroidal anti-inflammatory drug and said disintegrant are combined and then heated together until said non-steroidal anti-inflammatory is fully molten.

25. The process according to claim 21, wherein said drug and said disintegrant are extruded.

26. The process according to claim 25, wherein said drug and said disintegrant are extruded in a twin-screw extruder.

27. The process according to claim 21, wherein the granules are combined with an extra-granular component comprising a lubricant and silicon dioxide prior to compression into tablets.

28. The process according to claim 21, further comprising combining a diluent with the disintegrant and the drug in fully molten form.

29. The process according to claim 28, further comprising combining a surfactant with said diluent and said disintegrant.

30. A method for treating pain and/or inflammation and/or fever comprising administering a composition according to claim 1 to a mammal in need thereof.

31. A compressed tablet composition comprising:
   a) a granular component comprising a plurality of solidified melt granules of a non-steroidal anti-inflammatory drug having a melting point in the range of 30-300° C., wherein a disintegrant is uniformly dispersed therein; wherein said non-steroidal anti-inflammatory drug is present as a continuous phase within the granules obtainable by combining the disintegrant with said non-steroidal anti-inflammatory drug wherein said nonsteroidal anti-inflammatory drug is fully molten, wherein the tablet composition further comprises
   b) silicon dioxide present in an amount of 0.05 to 5.0% by weight of the composition, and
   wherein the non-steroidal anti-inflammatory drug is 60-97% by weight of the tablet composition.

32. The compressed tablet composition according to claim 31 wherein the silicon dioxide is present as an extra-granular component.

33. The compressed tablet composition according to claim 32 wherein the extra-granular component further comprises a lubricant.

34. The compressed tablet composition according to claim 31 wherein the granular component further comprises a surfactant.

35. The compressed tablet composition according to claim 32 wherein
   a) said granular component is 60-99.95% by weight of the composition, and said disintegrant is 0.05-1 parts by weight per part by weight of nonsteroidal anti-inflammatory drug; and
   b) said extra-granular component is 0.05-40% by weight of the composition.

36. The compressed tablet composition according to claim 31, wherein the non-steroidal anti-inflammatory drug is selected from the group consisting of ibuprofen, flurbiprofen, ketoprofen, naproxen and enantiomers thereof.

37. The compressed tablet composition according to claim 31, wherein the non-steroidal anti-inflammatory drug is an ibuprofen medicament.

38. The compressed tablet composition according to claim 31, wherein the disintegrant is selected from the group consisting of sodium starch glycolate and croscarmellose sodium.

39. The compressed tablet composition according to claim 31, wherein said silicon dioxide is present at 0.1-3% by weight of the composition.

40. The compressed tablet composition according to claim 31, further comprising diluent which is present at 0.1-20% by weight of the composition.

41. The compressed tablet composition according to claim 31, wherein the granular component comprises 70-95% non-steroidal anti-inflammatory drug by weight of the granular component.

42. The compressed tablet composition according to claim 37, wherein the composition comprises
   a) 90-99.95% granular component by weight of the composition, said granular component comprising solidified melt granules of ibuprofen incorporating croscarmellose sodium uniformly dispersed therein, said ibuprofen being present in an amount of 70-99% by weight of the composition, said croscarmellose sodium being present in an amount of 1-25% by weight of the composition, and further comprising
   b) 0.05-10% extra-granular component by weight of the composition, wherein said extra-granular component comprises:
      (i) 0.1-3% lubricant by weight of the composition; and
      (ii) 0.05-2% silicon dioxide by weight of the composition.

43. The compressed tablet composition according to claim 42, wherein the solidified melt granules further comprise a diluent uniformly dispersed therein, and the diluent is present in an amount of up to 20% by weight of the composition.

44. The compressed tablet composition according to claim 43, wherein the granular component consists essentially of ibuprofen, croscarmellose sodium and a diluent selected from the group consisting of microcrystalline cellulose and a salt of an organic acid.

45. The compressed tablet composition according to claim 31, wherein said non-steroidal anti-inflammatory drug is ibuprofen in an amount of 70-95% by weight of the composition.

46. The compressed tablet composition according to claim 31, wherein said disintegrant is croscarmellose sodium in an amount of 3-20% by weight of the composition.

47. The compressed tablet composition according to claim 33, wherein said extra-granular component consists essentially of silicon dioxide and a lubricant in a ratio of 1 part by weight silicon dioxide to 0.05-5 parts by weight lubricant.

48. The compressed tablet composition according to claim 40, wherein said granular component comprises:
   (i) 70-90% ibuprofen by weight of the composition;
   (ii) 8-20% croscarmellose sodium by weight of the composition; and
   (iii) 0-20% diluent by weight of the composition;
   and further comprising an extra-granular component comprising:
   (iv) 0.5-2% stearic acid or a salt thereof by weight of the composition; and
   (v) 0.1-2.5% silicon dioxide by weight of the composition, wherein the sum of components (i) to (v) being greater than 99% by weight of the composition.

49. A compressed tablet composition comprising:
   a granular component comprising a plurality of solidified melt granules of a non-steroidal anti-inflammatory drug having a melting point in the range of 30-300° C., wherein a disintegrant is uniformly dispersed therein; wherein all of the non-steroidal anti-inflammatory drug within the granules is present as a single continuous phase, the tablet composition comprises silicon dioxide present in an amount of 0.05-5.0% by weight of the composition, the silicon dioxide is present as an extra-granular component, and wherein the non-steroidal anti-inflammatory drug is 60-97% by weight of the tablet composition.

50. A compressed tablet composition comprising:
   a) a granular component comprising a plurality of solidified melt granules of a non-steroidal anti-inflammatory drug having a melting point in the range of 30-300° C., wherein a disintegrant is uniformly dispersed therein; wherein said non-steroidal anti-inflammatory drug is present as a continuous phase within the granules obtainable by combining the disintegrant with said non-steroidal anti-inflammatory drug wherein said nonsteroidal anti-inflammatory drug is fully molten, wherein the tablet composition further comprises b) an extra-granular component comprising silicon dioxide present in an amount of 0.05 to 5.0% by weight of the composition, wherein the non-steroidal anti-inflammatory drug is 60-97% by weight of the tablet composition.

51. The compressed tablet composition according to claim 1, wherein said disintegrant is uniformly dispersed into said non-steroidal anti-inflammatory drug while said non-steroidal anti-inflammatory drug is in molten form.

52. The compressed tablet composition according to claim 1, further comprising a salt of an organic acid.

53. The compressed tablet composition according to claim 52, wherein the salt of an organic acid is sodium citrate.

* * * * *